US008450629B2

(12) United States Patent
Pitcher

(10) Patent No.: US 8,450,629 B2
(45) Date of Patent: May 28, 2013

(54) METHOD OF PRODUCING MOLYBDENUM-99

(75) Inventor: Eric John Pitcher, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 91 days.

(21) Appl. No.: 13/104,698

(22) Filed: May 10, 2011

(65) Prior Publication Data

US 2011/0272272 A1 Nov. 10, 2011

Related U.S. Application Data

(60) Provisional application No. 61/333,128, filed on May 10, 2010.

(51) Int. Cl.

| | |
|---|---|
| ***C01G 39/00*** | (2006.01) |
| ***A61K 103/10*** | (2006.01) |
| ***A61K 33/40*** | (2006.01) |
| ***B01J 47/14*** | (2006.01) |
| ***B01J 41/00*** | (2006.01) |

(52) U.S. Cl.

USPC ........... 204/157.21; 423/2; 376/186; 376/189

(58) Field of Classification Search

USPC ................... 204/157.21; 376/186, 189; 423/2

See application file for complete search history.

(56) References Cited

U.S. PATENT DOCUMENTS 2,161,985 A * 6/1939 Szilard .......................... 376/189
3,320,033 A * 5/1967 Goren ............................. 423/54
3,382,152 A * 5/1968 Lieberman et al. ........... 376/186
3,607,008 A * 9/1971 Chiola et al. .................... 423/54
3,922,231 A * 11/1975 Carlin et al. ...................... 423/2
4,041,317 A * 8/1977 Morcos et al. ................ 376/186
4,094,953 A * 6/1978 Hadi et al. .................... 376/186
4,176,158 A * 11/1979 Laidler et al. ..................... 423/2
4,981,658 A * 1/1991 Ali et al. ........................... 423/2
5,508,010 A * 4/1996 Sameh et al. ...................... 423/2
5,603,834 A * 2/1997 Rogers et al. ................. 210/638
5,764,715 A * 6/1998 Maenchen et al. ......... 250/492.3
5,774,782 A * 6/1998 Mirzadeh et al. ................. 423/2
5,802,438 A * 9/1998 Bennett et al. .................... 423/2
5,874,811 A * 2/1999 Finlan et al. .................. 315/502
7,796,720 B1 * 9/2010 Rubbia ......................... 376/187
8,328,900 B2 * 12/2012 Bednarski et al. .............. 423/54
2005/0058839 A1 * 3/2005 Moller et al. ...................... 423/2
2006/0023829 A1 * 2/2006 Schenter et al. .............. 376/190
2009/0060812 A1 * 3/2009 Schenter et al. ......... 204/157.21
2009/0274258 A1 * 11/2009 Holden et al. ................ 376/190

OTHER PUBLICATIONS

Pitcher, "Analysis of Molbdenum-99 Production Capability in the Materials Test Station," available on-line at http://www-pub.iaea.org/MTCD/publications/PDF/P1433_CD/datasets/papers/ads_et-08.pdf?bcsi-ac-2160f1cfec5c399f=1EA310E3000001027jENKO0w/jq0EX/a2mq+1YuNWV5dNwAAAgEAAODyzwCEAwAABAAAAILeXAA=.*

(Continued)

*Primary Examiner* — Keith Hendricks
*Assistant Examiner* — Colleen M Raphael
(74) *Attorney, Agent, or Firm* — Juliet Ann Jones; Samuel L. Borkowsky

(57) ABSTRACT

Method of producing molybdenum-99, comprising accelerating ions by means of an accelerator; directing the ions onto a metal target so as to generate neutrons having an energy of greater than 10 MeV; directing the neutrons through a converter material comprising techentium-99 to produce a mixture comprising molybdenum-99; and, chemically extracting the molybdenum-99 from the mixture.

7 Claims, 2 Drawing Sheets

OTHER PUBLICATIONS

Pitcher, "Analysis of Molybdenum-99 Production Capability in the Materials Test Station," Los Alamos National Laboratory, International Topical Meeting on Nuclear Research Applications and Utilization of Accelerators, Vienna, Austria, May 4-8, 2009.*
Reimer et al, "Neutron induced reaction cross sections for the radioactive target nucleus 99Tc," Nuclear Physics A 815 (2009) pp. 1-17.*
Qaim, "Nuclear reaction cross-sections for 14.7 MeV neutrons on 99Tc," J. of Inorganic and Nuclear Chemistry, vol. 35, issue 11, Nov. 1973, pp. 3669-3575 (Abstract only).*
Ichikawa, "The Isolation of Technetium by Coprecipitation or Anion Exchange," Bull. Chem. Soc. Japan vol. 32 (1959), pp. 1126-1129.*
Nabardi et al, "A Closed System for Extraction of Injectable Pertechnetate from Molybdenum-99," Intl. J. Appl. Radia. Isot., vol. 33 (1982), pp. 473-474.*
Van der Walt et al, "The isolation of 99Mo from fission material for use in the 99Mo/99mTc generator for medical use," Radiochim. Acta, vol. 92 (2004), pp. 251-257.*
Sabel'nikov et al, "Preparation of 99Mo and 99mTc by 100Mo(gamma, n) Photonuclear Reaction on an Electron Accelerator, MT-25 Microtron," Radiochemistry, vol. 48, No. 2, (2006) pp. 191-194.*

* cited by examiner

METHOD OF PRODUCING MOLYBDENUM-99

CROSS REFERENCE TO RELATED APPLICATION

This application claims the benefit of priority of U.S. Provisional Patent Application 61/333,128, filed May 10, 2010, and is incorporated by reference herein in its entirety.

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to economically efficient method of producing molybdenum-99, using as a starting material technetium-99.

BACKGROUND OF THE INVENTION

Molybdenum-99 (Mo-99) is the radioactive parent of Technecium-99m (Tc-99m), a metastable radioisotope commonly used in medical procedures. Currently, the predominant production mechanism of molybdenum-99 is by fission of U-235, which produces a high-level waste (HLW) stream. Alternative, HLW-free mechanisms have been proposed, but most of these involve targets of isotopically-enriched molybdenum isotopes (e.g., 98Mo(n,g)99Mo or 100Mo(g,n) 99Mo), and have two drawbacks. First, production of the isotopically enriched targets is expensive. Second, the Mo-99 material has very low specific activity, which complicates chemical extraction of the Tc-99m from the molybdenum parent material.

The only reactor in North America which produces Mo-99 is nearing the end of its life, and the United States finds itself relying more heavily on overseas suppliers for this important medical isotope. Technetium-99 is utilized in approximately 70% of all medical procedures in the US that involve medical isotopes. Thus, a critical need has arisen for economical Mo-99 production sources within North America, which preferably do not create a high-level waste stream.

SUMMARY OF THE INVENTION

The method of the present invention utilizes the ground state of technetium, Tc-99 as a converter material that undergoes nuclear reactions to produce Mo-99. Technetium-99 does not exist in nature, but abundant supplies exist in spent nuclear fuel.

The method of the present invention has the advantage of not only avoiding the generation of additional high-level waste, but uses as a source of Tc-99 existing high-level waste which is in storage and for which no approved disposal methods exist. Thus, isotopically pure Tc-99 is readily available in sufficient quantity, and can also be recycled as converter material multiple times.

The following describes one non-limiting embodiment of the present invention.

According to one embodiment of the present invention, a method of producing molybdenum-99 is provided, comprising accelerating ions by means of an accelerator; directing the ions onto a metal target so as to generate neutrons having an energy of greater than 10 MeV; directing the neutrons through a converter comprising technetium-99 to produce a mixture comprising molybdenum-99; and, chemically extracting the molybdenum-99 from the mixture.

DETAILED DESCRIPTION OF THE INVENTION

The present invention describes a novel method for producing Mo-99 whereby high-energy neutrons irradiate a technetium-99 converter material, which in turn excites the $^{99}$Tc (n,p)$^{99}$Mo reaction. Traditionally, the production of neutrons has been achieved using a nuclear reactor. However, neutrons produced in a nuclear reactor have energies below the threshold energy needed to excite the $^{99}$Tc(n,p)$^{99}$Mo reaction and are therefore unsuitable sources of neutrons for this application. However, accelerated ions hitting a metallic target can produce neutrons having sufficient energy to excite the $^{99}$Tc (n,p)$^{99}$Mo reaction. The neutrons created in this way exit the metallic target and pass into a converter comprising Tc-99. Thus, by using a converter comprising Tc-99, in combination with an accelerator-driven neutron source, this limitation may be successfully overcome.

Figure 1:
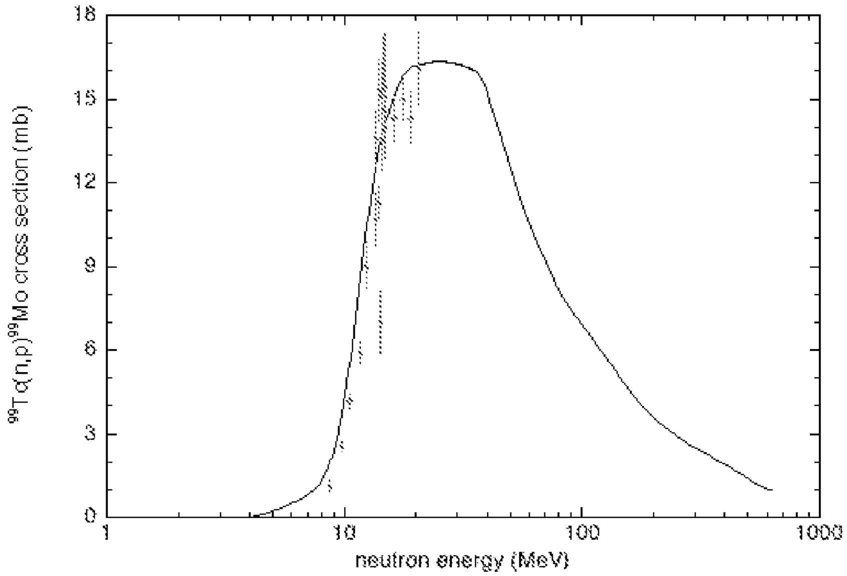
FIG. 1 depicts the predicted cross section for the $^{99}$Tc(n,p)$^{99}$Mo reaction, with the y-axis representing the probability of nuclear interaction in units of millibarns (mb) and the x-axis representing the incident neutron energy in megaelectron-volts (MeV).

According to one embodiment of the method of the present invention, ions are accelerated by means of an accelerator, and directed onto a metal target. The ions may be accelerated by a linear accelerator, or alternatively by a cyclotron. The accelerator may use warm (room temperature) accelerating structures, or superconducting (very low temperature) structures. The ions should have an energy greater than 10 MeV, alternatively of from about 10 MeV to about 300 MeV, and alternatively from about 20 MeV to about 100 MeV (see FIG. 1). In theory, any ion having sufficient energy may be used, and in one embodiment, the ions are deuterons.

The ions are then directed toward a metal target, which is capable, upon impact of the ions, of generating neutrons having an energy greater than 10 MeV. The material used for the metal target depends on the accelerated ion and its energy. In one embodiment, where the accelerator accelerates deuterons to an energy in the range of 20 to 100 MeV, the metal target is solid beryllium. In another embodiment, the metal target is lithium.

The generated neutrons are then directed onto a converter material comprising Tc-99, which then induces nuclear reactions, some of which produce Mo-99. In one embodiment, the neutrons are directed through the converter for a period of time comprising from about 1 day to about 5 days. The TC-99 in the target may be in the form of solid technetium metal, pertechnetate ($HTcO_4$), a pertechnetate salt, or combinations thereof. Typically, in order to use a pertechnetate salt (e.g., sodium or ammonium pertechnetate), the temperature of the target should be maintained below about 100° C. The Tc-99 is situated immediately behind the metal target, and is in the form of either a solid chunk of metal or in a container filled with Tc metal powder, or a powder comprising pertechnetate or pertechnetate salt. Virtually all Tc-99 on earth is the product of the nuclear fission; thus, in one embodiment, the Tc-99 is derived from spent nuclear fuel from a nuclear reactor.

Figure 2:
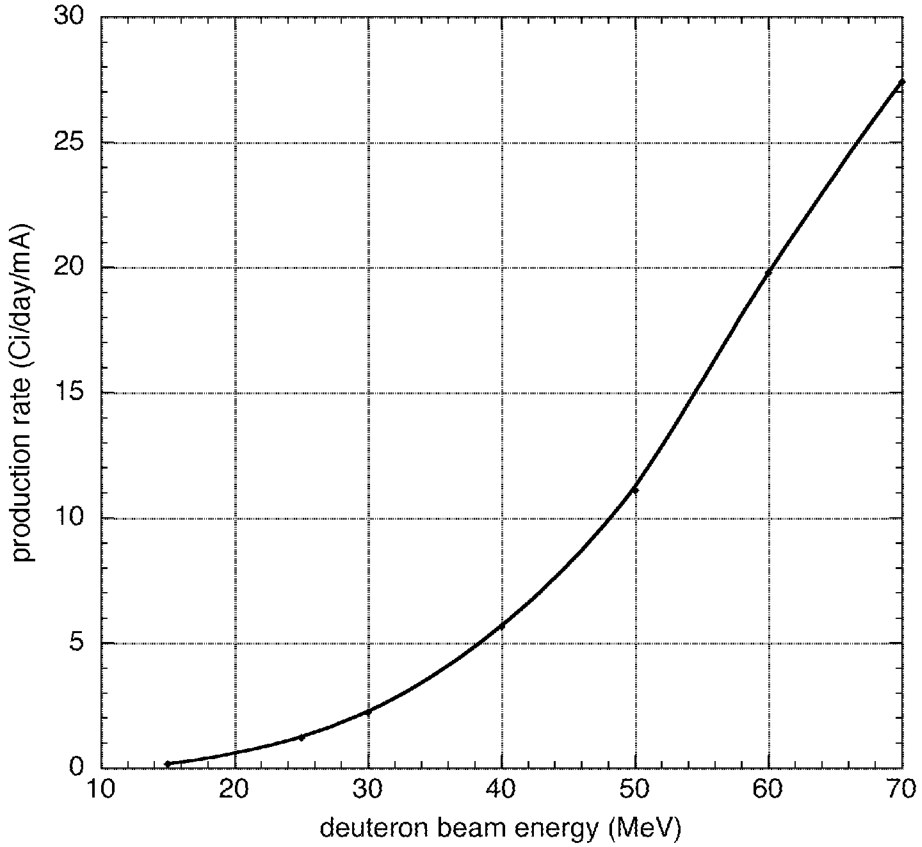
FIG. 2 shows the Mo-99 instantaneous production rate in curies per day per milliamp of deuteron beam current (Ci/day/mA) (y-axis) vs. deuteron beam energy in MeV (x-axis) (decay during production not accounted for).

The Mo-99 is then extracted from the mixture. In one embodiment, the extraction is a chemical extraction. In one embodiment, extraction results in substantially isotopically pure Mo-99, where "substantially" is understood to mean greater than about 90%. FIG. 2 shows the dependence of Mo-99 yield on deuteron beam energy.

In one embodiment, the chemical extraction may be performed as follows. After irradiation, the converter material comprising a mixture of Tc-99 with a trace amount of Mo-99 may be dissolved in a basic solution of sodium or ammonium hydroxide having a pH of from about 10 to about 11. The solution is passed through a strong-base anion exchange resin, where the molybdate anion, $MoO_4^{2-}$, is captured selectively and the pertechnetate anion ($TcO_4^-$), which is not held as strongly, passes through the column and is recycled to make a new target. Optionally, an additional cycle of elution from the first column and sorption on another anion exchange column may be performed. The molybdate captured on the final column becomes a source for producing Tc-99m as the pertechnetate, which can be eluted from the column for use in medical procedures.

In all embodiments of the present invention, all percentages are by weight of the total composition, unless specifically stated otherwise. All ratios are weight ratios, unless specifically stated otherwise. All ranges are inclusive and combinable. All numerical amounts are understood to be modified by the word "about" unless otherwise specifically indicated. All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing molybdenum-99, comprising:

a) accelerating ions by means of an accelerator;

b) directing the ions onto a metal target so as to generate neutrons having an energy of greater than 10 MeV;

c) directing the neutrons through a converter material comprising technetium-99 to produce a mixture comprising molybdenum-99; and, d) chemically extracting the molybdenum-99 from the mixture by dissolving the mixture in a basic solution of sodium hydroxide or ammonium hydroxide having a pH of from about 10 to about 11, and passing the resulting solution through an strong-base anion exchange resin wherein molybdate anion, $MoO_4^{2-}$ is captured selectively and pertechnetate anion, $TcO_4^-$ passes through the resin, thereby producing molybdenum-99.

2. The method of claim 1, wherein the metal target comprises metallic beryllium, lithium, or combinations thereof.

3. The method of claim 1, wherein the technetium-99 is in the form of solid technetium metal, pertechnetate, a pertechnetate salt, or combinations thereof.

4. The method of claim 1, wherein the accelerator is a cyclotron or a linear accelerator.

5. The method of claim 1, wherein the accelerated ions are deuterons.

6. The method of claim 1, wherein the technetium-99 is derived from spent nuclear fuel.

7. The method of claim 1, wherein the molybdenum-99 is substantially isotopically pure, wherein substantially means greater than about 90% isotopically pure.

* * * * *